United States Patent
Kawanaka et al.

(10) Patent No.: US 9,756,853 B2
(45) Date of Patent: Sep. 12, 2017

(54) SOLID PESTICIDAL FORMULATION

(71) Applicant: Sumitomo Chemical Company, Limited, Tokyo (JP)

(72) Inventors: Hideo Kawanaka, Takarazuka (JP); Naoya Akizuki, Kasai (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/903,918

(22) PCT Filed: Jul. 7, 2014

(86) PCT No.: PCT/JP2014/068647
§ 371 (c)(1),
(2) Date: Jan. 8, 2016

(87) PCT Pub. No.: WO2015/005487
PCT Pub. Date: Jan. 15, 2015

(65) Prior Publication Data
US 2016/0157480 A1 Jun. 9, 2016

(30) Foreign Application Priority Data
Jul. 12, 2013 (JP) ................................. 2013-146104

(51) Int. Cl.
*A01N 25/12* (2006.01)
*A01N 43/88* (2006.01)
*A01N 47/40* (2006.01)

(52) U.S. Cl.
CPC ............. *A01N 25/12* (2013.01); *A01N 43/88* (2013.01); *A01N 47/40* (2013.01)

(58) Field of Classification Search
CPC ........ A01N 47/40; A01N 25/12; A01N 43/88; A01N 51/00
See application file for complete search history.

(56) References Cited

U.S. PATENT DOCUMENTS

| | | | |
|---|---|---|---|
| 3,708,573 A | 1/1973 | Yoshinaga et al. | |
| 5,254,337 A * | 10/1993 | Marcus | B01J 20/18 423/335 |
| 5,576,007 A | 11/1996 | Ikeda et al. | |
| 6,432,476 B1 | 8/2002 | Corma Canos et al. | |
| 2002/0134239 A1* | 9/2002 | Tang | B01J 20/183 95/90 |
| 2006/0008493 A1 | 1/2006 | Jadhav et al. | |
| 2006/0111242 A1* | 5/2006 | Muller | A01N 25/12 504/361 |

FOREIGN PATENT DOCUMENTS

| | | |
|---|---|---|
| EP | 0579834 A1 | 1/1994 |
| EP | 1064843 A1 | 1/2001 |
| JP | H04327502 A | 11/1992 |
| JP | 2002505347 A | 2/2002 |
| WO | 2006008617 A2 | 1/2006 |

OTHER PUBLICATIONS

Cheng et al., Aerosol and Air Quality Research, vol. 7. No. 2, pp. 205-220, 206 (2007).*
English translation of International Search Report and Written Opinion issued Sep. 2, 2014 in International Application No. PCT/JP2014/068647.
Office Action issued on Jul. 21, 2016 in CN Application No. 201480039263.1.
Supplemental European Search Report and Written Opinion issued on Nov. 29, 2016 in EP Application No. 14822970.1.
Sopkova et al., "An Insecticide Stabilized by Nature Zeolite", Journal of Thermal Analysis and Calorimetry, vol. 53, No. 2, pp. 477-485 (Aug. 1, 1998).
Sopkova et al.,"About the Inclusion of an Insecticide in Zeolitic Materials", Journal of Thermal Analysis., vol. 46, No. 2, pp. 471-478 (Feb. 1, 1996).
Zhang et al., "Controlled Release of Paraquat from Surface-Modified Zeolite Y", Microporous and Mesoporuous Materials, Elsevier, vol. 88, No. 1-3, pp. 312-318 (Jan. 21, 2006).
Ramesh et al., "Zeolites and Their Potential Uses in Agriculture" In: "Advances in Agronomy", vol. 113, pp. 219-241 (Jan. 1, 2011).
Office Action issued Apr. 12, 2017 in CN Application No. 201480039263.1.

* cited by examiner

*Primary Examiner* — Robert Cabral
(74) *Attorney, Agent, or Firm* — Panitch Schwarze Belisario & Nadel LLP

(57) ABSTRACT

A sustained-release solid pesticidal formulation comprising pesticidal active ingredient and a zeolite as specified below, wherein the solubility in water of the pesticidally active ingredient is 100 to 100000 mg/L, and wherein the zeolite has $SiO_2$ and $Al_2O_3$ in total of 90% by weight or more to the weight of the zeolite, has molar ratio of $SiO_2/Al_2O_3$ of 4 or more, and has an average particle size of 10 μm or less.

7 Claims, 1 Drawing Sheet

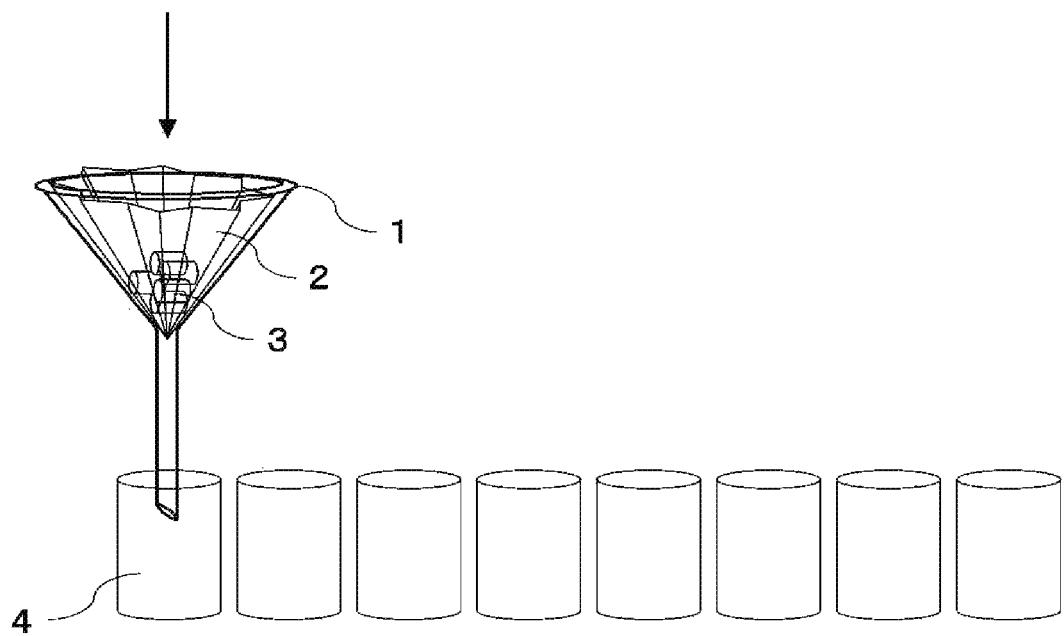

SOLID PESTICIDAL FORMULATION

CROSS-REFERENCE TO RELATED APPLICATION

This application is a Section 371 of International Application No. PCT/JP2014/068647, filed Jul. 7, 2014, which was published in the Japanese language on Jan. 15, 2015, under International Publication No. WO 2015/005487 A1, and the disclosure of which is incorporated herein by reference.

TECHNICAL FIELD

The present invention relates to a solid pesticidal formulation.

BACKGROUND ART

As recent aging of farmers and the like, under the circumstance that labor-saving farm work is needed, a sustained-release formulation which releases a pesticidal active ingredient gradually has attracted attention. The sustained-release formulation had developed as the purpose of reducing injury to crops and improving a residual effect, and as such sustained-release formulation, for example, a coated pesticidal granule which a pesticidal granule containing a pesticidal active ingredient was coated with a resin film were known (for example, refer to JPH11-5704-A), but as such coated pesticidal granule, there is still room for improvement in views of manufacturing costs and environmental aspects, because it needed a coating process, and was worried about the resin film remains for a long-term.

As for the sustained-release pesticidal solid formulation except for above-mentioned coated pesticidal formulation, a solid pesticidal formulation comprising a pesticidal active ingredient and a porous carrier having adsorption ability was known, but depending on the pesticidal active ingredient and the porous carrier to be used, the adsorption ability and retainability of the porous carrier to the pesticidal active ingredient was not sufficient. So, it was disclosed that it could be obtained desired sustained-release by further comprising a hydrophobic material such as a wax (for example, refer to JP2011-140452-A). As described above, conventional solid pesticidal formulation comprising a pesticidal active ingredient and a porous carrier having adsorption ability could not avoid using other materials to obtain desired sustained-release.

An object of the present invention is to provide a novel sustained-release type solid pesticidal formulation without coating with a resin film or blending a hydrophobic material such as a wax.

DISCLOSURE OF THE INVENTION

The present inventors have studied to find a solid pesticidal formulation to solve above-mentioned object.

As a result, they found a solid pesticidal formulation in which agrochemical active ingredient (s) are formulated into solid formulation in combination with a zeolite having specified ranges of total amount of $SiO_2$ and $Al_2O_3$, molar ratio of $SiO_2/Al_2O_3$, and a particle size can sustained-release of a pesticidal active ingredient contained in the formulation.

That is, the present inventions are as following [1] to [4].

[1] A sustained-release solid pesticidal formulation comprising a pesticidally active ingredient and a zeolite defined below, wherein the solubility in water of the pesticidally active ingredient is 100 to 100000 mg/L, and wherein the zeolite has $SiO_2$ and $Al_2O_3$ in total of 90% by weight or more to the weight of the zeolite, has molar ratio of $SiO_2/Al_2O_3$ of 4 or more, and has an average particle size of 10 μm or less (hereinafter referred to as the present formulation of the invention).

[2] The sustained-release solid pesticidal formulation according to [1], wherein the pesticidally active ingredient is a neonicotinoid type insecticidally active ingredient.

[3] The sustained-release solid pesticidal formulation according to [2], wherein the neonicotinoid type insecticidally active ingredient is at least one neonicotinoid type insecticidally active ingredient selected from the group consisting of clothianidin, thiamethoxam, dinotefuran, imidacloprid, acetamiprid and thiacloprid.

[4] The sustained-release solid pesticidal formulation according to any one of [1] to [3], wherein the zeolite is Y type zeolite.

[5] The sustained-release solid pesticidal formulation according to any one of [1] to [4], which contains 0.01 to 30% by weight of the pesticidally active ingredient per 100% by weight of the formulation.

[6] The sustained-release solid pesticidal formulation according to any one of [1] to [5], which contains 0.1 to 20% by weight of the zeolite defined in [1] per 100% by weight of the formulation.

[7] The sustained-release solid pesticidal formulation according to any one of [1] to [6], wherein the ratio by weight of the pesticidally active ingredient and the zeolite defined in [1] is 1:0.1 to 1:30.

According to the present invention, a novel sustained-release type solid pesticidal formulation can be provided. The sustained-release type solid pesticidal formulation of the present invention can sustain release of the agrochemical active ingredient(s) by using a specific zeolite, without coating with a resin film or blending a hydrophobic material such as a wax. Therefore, comparing to conventional coated pesticidal formulations, the sustained-release type solid pesticidal formulation of the present invention can be easily manufactured and can save manufacturing costs.

BRIEF DESCRIPTION OF THE DRAWINGS

[Drawing 1] The schematic of a method of testing the elution of pesticidal active ingredient(s) included in the solid pesticidal formulation (The test Example 1).

MODE FOR CARRYING OUT THE INVENTION

The solid pesticidal formulation of the present invention comprises pesticidal active ingredient(s) (hereinafter, in some cases, referred to as the component a) and a zeolite defined below, wherein solubility in water at 20° C. of the pesticidal active ingredient is 100 to 10000 mg/L, and the zeolite has $SiO_2$ and $Al_2O_2$ in total of 90% by weight or more to the weight of the zeolite, has molar ratio of $SiO_2/Al_2O_3$ of 4 or more, and has an average particle size of 10 μm or less.

In some cases, hereinafter, the zeolite having $SiO_2$ and $Al_2O_3$ in total of 90% by weight or more to the weight of the zeolite, molar ratio of $SiO_2/Al_2O_3$ of 4 or more, and an average particle size of 10 μm or less is referred to as the component b.

The component a is exemplified by an insecticidal active ingredient, a fungicidal active ingredient, a herbicidal active ingredient and a plant growth controlling active ingredient, and solubility in water at 20° C. of the component a included in the present formulation of the invention is 100 to 10000 mg/L.

The insecticidal active ingredient is exemplified by BPMC, DCIP, DDVP, DMTP, NAC, acetamiprid, imicyafos, imidacloprid, cadusafos, clothianidin, chloropicrin, dinotefuran, dimethoate, thiocyclam hydrogen oxalate, cyromazine, thiacloprid, hiamethoxam, pymetrozine, flonicamid, fosthiazate, malathion and methomyl.

The fungicidal active ingredient is exemplified by IBP, etridiazole, cymoxanil, dazomet, tetraconazole, tricyclazole, pyroquilon, ferimzone, furametpyr, propiconazole, probenazole, pefurazoate, myclobutanil, metalaxyl-M and metominostrobin.

The herbicidal active ingredient is exemplified by 2,4-PA, PAC, S-metolachlor, asulam, alachlor, isouron, imazapyr, ethoxysulfuron, cyanazine, dimethenamid, dimethenamid-P, simetryn, sethoxydim, terbacil, thifensulfuron-methyl, tebuthiuron, tepraloxydim, triclopyr, nicosulfuron, halosulfuron, bispyribac-sodium, flazasulfuron, fluazifop, fluazifop-P, flucetosulfuron, bromacil, benfuresate, mecoprop-P, mesotrione, metamitron, metolachlor, metribuzin and molinate.

The plant growth controlling active ingredient is exemplified by 1-naphthylacetic acid, indolebutyric acid, ethychlozate, dichlorprop, trinexapac-ethyl, flurprimidol and prohexadione.

The molecular weight of the component a is usually 150 to 500, preferably 200 to 400, more preferably 200 to 300.

The component a may be a solid or liquid at 25° C., in the viewpoint of manufacturing efficiency, the solid is preferable. And the present formulation of the invention can be contain plural kinds of pesticidal active ingredients as the component a, in such case, solubility in water at 20° C. of each of pesticidal active ingredients is 100 to 10000 mg/L.

In case that the component a is a solid pesticidal active ingredient at 25° C., a ground product previously grounded the pesticidal active ingredient itself or a mixture of the pesticidal active ingredient and a solid carrier (in some cases, hereinafter, referred to as the component c). In such case, the ground product is grounded, so that the particle diameter of the grounded product is usually 1 to 100 micrometer, preferably 1 to 50 micrometer. A solid carrier at 25° C. to be used in the field of solid pesticidal formulation such as a powder, a granule, a powder granule, and the like can be used as the component c, for example, exemplified by an organic acid (citric acid, succinic acid, maleic acid, and the like) or a salt thereof, a water soluble carrier such as urea sugar [lactose, glucose, sucrose and the like] and the like, vegetable powder (soy flour, tobacco powder, wheat flour, wood flour and the like), a mineral or an inorganic powder (clays such as kaolin, bentonite, acid clay, clay and the like, talc such as talcum powder, pagodite powder and the like, silicas such as diatomaceous earth, mica powder and the like, aluminum, powdery sulfur, activated carbon, potassium chloride, ammonium sulfate, sodium hydrogen carbonate, sodium sulfate, calcium carbonate, magnesium sulfate and the like), and zeolite other than the component b (Zeolite SK7A (trade name, NITTO FUNKA KOGYO K.K.), MIZU-KASIEVES (trade name, MIZUSAWA INDUSTRIAL CHEMICAL, LTD.) and the like), each of them can be used individually, or blended with one or more of other kinds.

When a neonicotinoid insecticidal active ingredient having solubility in water at 20° C. of 100 to 10000 mg/L as the component a is contained in the present formulation of the invention, the component a is effectively sustained-released. Such neonicotinoid insecticidal active ingredient is exemplified by clothianidin, thiamethoxam, dinotefuran, imidacloprid, acetamiprid, thiacloprid and the like.

The present formulation of the invention contains usually 0.01 to 30% by weight, preferably 0.01 to 20% by weight, more preferably 0.1 to 15% by weight of the component a, per 100% by weight of in the present formulation of the invention.

The present formulation of the invention contains the component b. The component b is a crystalline aluminosilicates, and the aluminosilicates contains $SiO_2$ and $Al_2O_3$. The total contents of $SiO_2$ and $Al_2O_3$ in the component b is 90% by weight or more, preferably 90 to 100% by weight, more preferably 90 to 95% by weight per 100% by weight of the component b, and the molar ratio of $SiO_2/Al_2O_3$ is usually 4 or more, preferably 4 to 40, more preferably in the range of from 4 to 25.

The total contents of $SiO_2$ and $Al_2O_3$ in the component b and the molar ratio of $SiO_2/Al_2O_3$ in the component b can be measured by using ZSX Primus II (X-ray fluorescence analyzer manufactured by Rigaku Corporation). In the present invention. The total contents of $SiO_2$ and $Al_2O_3$ means the amount of semi-quantitative value of $SiO_2$ and semi-quantitative value of $Al_2O_3$ analyzed by X-ray fluorescence analysis.

A particle size of the component b is usually 10 micrometer or less, preferably 1 to 8 micrometer, more preferably in the range of from 2 to 6.

In the present invention, particle sizes of each of the ground product grounded the mixture of the component a and the component c, and, the component b mean volume median diameter of each of them. The volume median diameter refers to a particle size corresponding to a cumulative frequency of 50% in a frequency distribution on volume basis. By using, for example, a laser diffraction particle size distribution analyzer, the particle size can be determined by wet measurement. In particular, an object to be measured is measured by using such analyzer in water as a dispersion medium. Example of the laser diffraction particle size distribution analyzer includes Mastersizer 2000 manufactured by Malvern Instruments.

A pore size of the component b is usually 5 to 10 Å, preferably in the range of from 6 to 9 Å.

The pore size of the component b can be measured by measurement of a pore size distribution obtained by an automatic gas/vapor adsorption amount measurement apparatus or an analysis of a diffraction pattern obtained by an x-ray diffraction apparatus. The automatic gas/vapor adsorption amount measurement apparatus is, for example, exemplified by BELSORP-18 (manufactured by BEL Japan, Inc.). The x-ray diffraction apparatus is, for example, exemplified by XRD-6100 (manufactured by Shimadzu. Corporation).

A specific surface area of the component b is usually 450 to 800 $m^2/g$, preferably in the range of from 500 to 750 $m^2/g$.

The specific surface area of the component b can be measured by following the BET multipoint method regulated in JIS R 1626-1996. In particular, a zeolite is pretreated before heating by using a pretreatment apparatus for an adsorption measurement, then, it can be measured by using a constant volume method with $N_2$ as an adsorbate and an automatic gas/vapor adsorption amount measurement apparatus. The a pretreatment apparatus for an adsorption measurement is, for example, exemplified by BELPREP-18 (manufactured by BEL Japan, Inc). The automatic gas/vapor adsorption amount measurement apparatus is, for example, exemplified by BELPREP-18 (manufactured by BEL Japan, Inc.)

The component b is preferably in faujasite type, more specifically, preferably in Y-type zeolite.

A structure of zeolite is, for example, can be measured by powder X-ray diffraction method. In particular, it can be measured by using X-ray diffraction analysis apparatus SmartLab (manufactured by Rigaku Corporation).

In the present invention, commercial products can be used as the component b. Such commercial products is, for example, exemplified by Abscents 1000 (manufactured by UNION SHOWA K.K.) and HiSiv 1000 (manufactured by UNION SHOWA K.K.).

The present formulation of the invention contains usually 0.1 to 20% by weight, preferably 0.5 to 15% by weight, more preferably 1.0 to 10% by weight of the component b in total, per 100% by weight of in the present formulation of the invention.

In the present formulation of the invention, a ratio of the component a to the component b containing therein is, by weight ratio, usually 1:0.1 to 1:30, preferably in the range of from 1:0.2 to 1:20.

The present formulation of the invention optionally can contain the component c. The component c is exemplified by as described above.

When the present formulation of the invention contains the component c, the contents of the component c in total is usually 10 to 99% by weight, preferably 30 to 98% by weight, more preferably 50 to 95% by weight per 100% of the present formulation of the invention.

Additionally, the present formulation of the invention optionally may contain surfactants (in some case, hereinafter, referred to as the component d). The component d is materials generally used as surfactants such as nonionic surfactants, anionic surfactants, cationic surfactants, amphoteric surfactants, and the like, and there is not especially limitation.

The nonionic surfactant is, for example, exemplified by polyoxyethylenealkylether, polyoxyethylenealkylarylether, polyoxyethylenestlphenolether, polyoxyethylenelanolin alcohol, polyoxyethylenealkylphenol formalin condensate, polyoxyethylene sorbitan fatty acid ester, polyoxyethyleneglyceryl monofatty acid ester, polyoxypropyleneglycol monofatty acid ester, polyoxyethylenesorbitol fatty acid ester, polyoxyethelene castor oil derivative, polyoxyethylene fatty acid ester, higher fatty acid glycerin ester, sorbitan fatty acid ester, sucrose fatty acid ester, polyoxyethylenepolyoxypropylene block copolymer, polyoxyethylene fatty acid amide, alkylolamide and polyoxyethylenealkylamine.

The anionic surfactant is, for example, exemplified by fatty acid sodium salts such as sodium palmitate and the like, ethercarboxylate sodium salts such as sodium polyoxyethyleneraurylether carboxylate and the like, higher fatty acid amino acid condensates such as sodium lauroyl sarcosinate, lauroylglutamic acid sodium salt and the like, higher alkyl sulfonates, higher fatty acid ester sulfonates such as laurc acid ester sulfonate and the like, dialkylsulfosuccinates such as dioctylsulfosuccinates and the like, higher amide sulfonates such as oleamide sulfonate and the like, alkylaryl sulfonates such as sodium dodecylbenzenesulfonate, sodium diisopropylnaphthalenesulfonate, and the like, alkylarylsulfonate formalin condensates, higher alcohol sulfates such as pentadecan-2-sulfate and the like, polyoxyethylenealkylphosphate ester salts such as dipolyoxyethylenedodecylether phosphate ester salts and the like, and salts of stylene maleic acid copolymer.

The cationic surfactants is, for example, exemplified by alkyl amine hydrochloride salts such as dodecyl amine hydrochloride salts and the like, tertialy ammoniun salts such as dodecyltrimethyl ammonium salts, alkyldimethylbenzyl ammonium salts, alkyl pyridinium salts, alkyl isoquinolinium salts, dialkyl morphonium salts, benzethonium chloride and polyalkylvinyl pyridinium salts.

The amphoteric surfactant is, for example, dialkylamino ethyl betaine, alkyldimethyl benzyl betaine, dialkylaminoethyl ethyl glycine and alkyl dimethylbenzyl glycine.

When the present formulation of the invention contains the component d, the content of the component d in total is usually 0.01 to 10% by weight, preferably 0.01 to 10% by weight, more preferably 0.5 to 3% by weight per 100% of the present formulation of the invention.

The present formulation may further include auxiliaries for formulation such as a binder, a disintegration agent, a flocculant, a lubricant, a pH adjusting agent, a stabilizer and a preservative.

When the present formulation of the invention contains auxiliaries, the content of auxiliaries in total is usually 0 to 30% by weight, preferably 0.1 to 20% by weight, more preferably 0.1 to 15% by weight per 100% of the present formulation of the invention.

The binder is, for example, exemplified by starch, soluble starch, dextrin, alpha-starch, sodium alginate, gum arabic, lignosulfonate, sodium carboxymethyl cellulose, methyl cellulose, ethyl cellulose, hydroxyethyl cellulose, hydroxypropyl cellulose, polyvinyl alcohol, and sodium polyacrylate. Among these, dextrin, alpha-starch and polyvinyl alcohol are preferable, and especially, dextrin is preferable. Each of these binders is used alone or in combination with one or more others.

When the binder is used, it can be used by preparing an aqueous solution of the binder and adding the aqueous solution into the other components, or by adding the binder as powder into the other components.

When the present formulation of the invention contains a binder, the content of binder in total is usually 1 to 15% by weight, preferably 1 to 10% by weight per 100% of the present formulation of the invention.

The form (formulation type) of the present formulation of the invention is dusts (dust, low drift dust, flow dust), granule and powder granule (micro granule, micro granule fine, fine granule), and can be manufactured by known manufacturing method. Then, in case that the present formulation of the invention is granule, it may be form of both water disintegrating granule and water non-disintegrating granule. In the present invention, water non-disintegrating granule means a granule having its disintegration time in water of 24 hours or more, and water disintegrating granule means a granule having its disintegration time in water of less than 24 hours.

A method for measuring disintegration time in water is, specifically, as follows.

At first, 50 mL of 3 degrees hard water is poured into petri dish of glass having its diameter of 9 cm and stand, and five test granules are set therein as substantially uniform. Then, the disintegration time in water can be obtained by measuring a period from setting test granules therein to disappearance of its original form.

Granules (water disintegrating granule and water non-disintegrating granule) of the present formulation of the invention can be obtained, for example, by mixing a pesticidal active ingredient and the component b, and as necessary, further mixing with a solid carrier, a surfactant and pesticidal auxiliaries, adding water, and keading, then, extruding granulation and followed by drying and, as necessary, grading, sizing and screening.

A kneading machine to be used in manufacturing a granule is, for example, exemplified by a kneader, a Nauta mixer and a Lodige mixer.

An extruding granulation is usually carried out by using the screen with hole its diameter of usually from 0.5 to 2.0 mmφ, and preferably from 0.7 to 1.5 mmφ.

An extrusion granulator is, for example, exemplified by a screw type extrusion granulator, a roll type extrusion granulator, a disc pelleter type extrusion granulator, a pellet mill type extrusion granulator, a basket type extrusion granulator, a blade type extrusion granulator, an oscillating type extrusion granulator, a gear type extrusion granulator and a ring die type extrusion granulator, and specifically exemplified by Twin dome Gran (manufactured by DALTON CO., LTD.) Single dome Gran (manufactured by DALTON CO., LTD.), Multi Gran (manufactured by DALTON CO., LTD.), Basket Ryuzer (manufactured by DALTON CO., LTD.), Pelleter Double (manufactured by DALTON CO., LTD.) and HATA-type granulator (HATA TEKKOSHO CO., LTD.).

An extrudate obtained by extrusion granulating can be dried, by using heat air of inlet of dryer at a temperature of from 0 to 90° C., preferably from 50 to 80° C. The dryer is exemplified by a fluidized bed dryer (manufactured by POWFWX Corporation).

An extrudate obtained by extrusion granulating and drying is screened so that a grain length is of usually from 0.5 to 6.0 mm, preferably in the range of from 0.7 to 4.0 mm. Here, the grain length means the maximum length to be indicated.

A method of grading and sizing is exemplified by a wet sizing method with before-drying granule by round shape granulator (trade name: Marumerizer, manufactured by DALTON CO., LTD.) of high speed rolling method, and dry sizing method with dried granule by cracking machine such as a pin mill When the present formulation of he invention is granules (water disintegrating granule and water non-disintegrating granule), it is preferable to contain a binder as pesticidal auxiliaries.

Powder granules (micro granule, micro granule fine, fine granule) of the present formulation of the invention can be obtained, for example, by mixing a pesticidal active ingredient and the component b, and as necessary, further mixing with a solid carrier, a surfactant and pesticidal auxiliaries, and extruding granulation and followed by sizing and screening so that the granule become desired particle size.

A method of sizing is, for example, exemplified by a method of sizing by using a sizing apparatus such as pin mill.

When the present formulation of the invention is powder granules (micro granule, micro granule fine, fine granule), it is preferable to contain a binder as pesticidal auxiliaries.

Dusts (dust, low drift dust, flow dust) of the present formulation of the invention can be obtained, for example, by mixing a pesticidal active ingredient and the component b, and as necessary, further mixing with a solid carrier, a surfactant and pesticidal auxiliaries, and as necessary, pulverizing.

A method of pulverizing is, for example, exemplified by a method of dry-pulverization by using a vertical jet pulverizer (trade name: SK jet-O-mill, SEISHIN ENTERPRISE Co., Ltd.) and high speed hammer mill (trade name: Atomizer, SEISHIN ENTERPRISE Co., Ltd.).

When the present formulation of the invention is dusts (dust, low drift dust, flow dust), it is preferable to contain a binder as pesticidal auxiliaries.

The present formulation of the invention is preferably granules (water disintegrating granule and water non-disintegrating granule) or powder granules (micro granule, micro granule fine, fine granule), to avoid expose operators to dusting and to save environmental influences by drift. In particular, the water disintegrating granule which can be disintegrated in a small quantity of water and adhered to soil, and became hard to flow away, is more preferable, because the pesticidal active ingredient is not only used effectively, but also environmental influence is minimized.

The present formulation of the invention is applied by a general application method of dusts, granules and powder granules.

As for dusts, they are applied by using, for example, a boom type blow head (pipeduster).

As for granules and powder granules, they are applied directly on hand, or using a granule applicator such as a knapsack granule applicator, a pipe granule applicator, an aerial granule applicator, a power applicator, a nursery box granule applicator, a tractor-loaded type granule applicator, a perforated hose attached granule applicator, a rice transplanter loaded granule applicator and the like.

By applying the present formulation of the present invention, harmful pests can be controlled. In this invention, pests mean harmful diseases and pests which can he controlled by the pesticidal active ingredient contained in the present formulation of the invention. And, the present formulation of the invention is used, as the pesticidal active ingredient contained therein or purpose of use, at crop land such as a paddy field, a dry paddy field, a nursery box, a farmland, an orchard, a mulberry field, a greenhouse and an open field, and non-crop land such as a forest, a turf, a golf course, a street tree, a road, a berm, a marsh, a pond, a reservoir, a river, a waterway and a sewer.

EXAMPLES

The present invention is further described in detail, but the present invention is not limited only these EXAMPLES.

First, Production Examples and Reference Production Examples are described.

Reference Production Example 1

70.0 parts of technical product of clothianidin (purity 98.9%, solubility in water 327 mg/L (20° C.), manufactured by SUMITOMO CHEMICAL Co., Ltd.) and 30.0 parts of clay (SHOKOZAN CLAY, SHOKOZAN MINING Co., Ltd.) are mixed, and followed by pulverizing with centrifugal mill (manufactured by RETSCH GmbH), to obtain pulverized product (hereinafter, referred to as clothianiddin fine powder; content of active ingredient 69.2% by weight, particle size 15.1 micrometer (measured value by Mastersizer 2000, wet measurement).

Production Examples 1 to 7 (Water Disintegrating Granule)

Raw materials described in the Table 1 are mixed at the weight ratio described in the Table 1, predetermined volume of water was added, then kneaded substance obtained by kneading the mixture was granulated by using Multi Gran (MG55 type; manufactured by DALTON CO., LTD.) in which a screen of 0.8 mmφ was loaded, and dried by fluidized bed dryer (LAB-1; manufactured by POWRWX Corporation), to obtain the Present Granules of the invention 1 to 7 of water disintegrating granule.

In addition, figures in the Table 1 means parts by weight, and "valance" means residual amount of 100 parts by weight of whole amount.

Tankaru NN200: potassium carbonate, manufactured by NITTO FUNKA KOGYO K.K.

barite: barium sulfate, manufactured by Neolite Kosan

TABLE 1

| | the Present Granules of the invention | | | | | | |
|---|---|---|---|---|---|---|---|
| | 1 | 2 | 3 | 4 | 5 | 6 | 7 |
| clothianidin fine powder | 0.72 | 0.72 | 0.72 | 0.72 | | | 14.57 |
| dinotefuran | | | | | 0.5 | | |
| thiamethoxam | | | | | | 0.5 | |
| Sorpol 5080 | 1.0 | 1.0 | 1.0 | 1.0 | 1.0 | 1.0 | |
| NEOCOL SWCP | | | | | | | 0.5 |
| Toxanon GR 31A | | | | | | | 2.0 |
| AKADAMA dextrin NDS | 4.0 | 4.0 | 4.0 | 4.0 | 4.0 | 4.0 | |
| BENTONITE HODAKA | 20.0 | 20.0 | 20.0 | 20.0 | 20.0 | 20.0 | |
| Kunigel V1 | | | | | | | 26.0 |
| urea | 8.0 | 8.0 | 8.0 | 8.0 | 8.0 | 8.0 | |
| ammonium sulfate | 5.0 | 5.0 | 5.0 | 5.0 | 5.0 | 5.0 | |
| RADIOLITE # 200 | 20.0 | 20.0 | 20.0 | 20.0 | 20.0 | 20.0 | |
| Zeolite SK7A | 3.2 | 3.2 | 3.2 | 3.2 | 3.2 | 3.2 | |
| Abscents 1000 | 1.0 | 3.0 | 5.0 | 10.0 | 3.0 | 3.0 | 5.0 |
| Tankaru NN200 | balance | balance | balance | balance | balance | balance | |
| barite | | | | | | | balance |
| Total | 100.0 | 100.0 | 100.0 | 100.0 | 100.0 | 100.0 | 100.0 |

Explanations of ingredients described in above Table 1 are described below.

dinotefuran: purity 99.0%, solubility in water 40000 mg/L (20° C.), manufactured by Wako Pure Chemical Industries, Ltd.

thiamethoxam: purity 99.0%, solubility in water 4100 mg/L (20° C.), manufactured by Wako Pure Chemical Industries, Ltd.

Sorpol 5080: polyoxyethylenetristyrylphenylether, manufactured by TOHO Chemical Industry Co., Ltd.

NEOCOL SWCP: dialkylsulfosuccinate, manufactured by DKS Co. Ltd.

Toxanon CR 31A: mixture of 43% by weight of polyacrylate and 57% by weight of water, Sanyo Chemical Industries, Ltd.

dextrin NDS: dextrin, manufactured by Nippon Starch Chemical Co., Ltd.

BENTONITE HODAKA: bentonite, manufactured by HOJUN Co., Ltd.

Kunigel V1: bentonite, manufactured by KUNIMINE INDUSTRIES CO., LTD.

urea: manufactured by Mitsui Chemicals, Inc.

ammoniun sulfate: manufactured by SUMITOMO CHEMICAL Co., Ltd.

RADIOLITE #200: burned diatomite, manufactured by Showa Chemical industry Co., Ltd.

Zeolite SK7A: mordenite type zeolite, total content of $SiO_2$ and $Al_2O_3$ 76.6% (measured value by ZSX Primus II), $SiO_2/Al_2O_3$ molar ratio 9.77, manufactured by NITTO FUNKA KOGYO K.K. Abscents 1000: Y-type zeolite, total content of $SiO_2$ and $Al_2O_3$ 92.5% (measured value by ZSX Primus II), $SiO_2/Al_2O_3$ molar ratio 4.9, particle size 4.2 micrometer (measured value by Mastersizer 2000, wet measurement), specific surface area 581 m$^2$/g (measured value by BELSORP-18, BET multipoint method), pore size 6.2 Å (measured by BELSORP-18, analyzing method: t method), manufactured by UNION SHOWA K.K.

Reference Production Examples 2 to 5 (Water Disintegrating Granule)

Raw materials described in the Table 2 are mixed at the weight ratio described in the Table 2, the Comparative granules 1 to 4 of water disintegrating granule were obtained in the same manner as described in Production Examples 1 to 7

In addition, figures in the Table 2 means parts by weight, and "valance" means residual amount of 100 parts by weight of whole amount.

TABLE 2

| | the Comparative Granule | | | |
|---|---|---|---|---|
| | 1 | 2 | 3 | 4 |
| clothianidin fine powder | 0.72 | 0.72 | | |
| dinotefuran | | | 0.5 | |
| thiamethoxam | | | | 0.5 |
| Sorpol 5080 | 1.0 | 1.0 | 1.0 | 1.0 |
| AKADAMA dextrin NDS | 4.0 | 4.0 | 4.0 | 4.0 |
| BENTONITE HODAKA | 20.0 | 20.0 | 20.0 | 20.0 |
| urea | 8.0 | 8.0 | 8.0 | 8.0 |
| ammoniun sulfate | 5.0 | 5.0 | 5.0 | 5.0 |
| RADIOLITE # 200 | 20.0 | 20.0 | 20.0 | 20.0 |
| Zeolite SK7A | 3.2 | | 3.2 | 3.2 |
| Mizuka Sieves EX122 | | 3.0 | | |
| Tankaru NN200 | balance | balance | balance | balance |
| Total | 100.0 | 100.0 | 100.0 | 100.0 |

Explanations of ingredients described in above Table 2 are described below.

Mizuka Sieves EX122: ZSM-5-type zeolite, total content of $SiO_2$ and $Al_2O_3$ 85.9% (measured value by ZSX Primus II), $SiO_2/Al_2O_3$ molar ratio 29.4, particle size 4.3 micrometer (measured value by Mastersizer 2000, wet measurement), specific surface area 420 m$^2$/g (BET)

Explanations of remaining ingredients are as described above.

Test Example 1

Elution Test

DRAWING 1 is the schematic of the present test. A pleated filter paper 2 having retained particle diameter of 1 micrometer (filter paper for quantitative analysis NO. 5C, manufactured by Advantec Co., Ltd.) was placed on the glass funnel 1 (caliber: 60 mmφ, stem diameter: 9 mmφ, length: 78 mm, manufactured by TOKYO RIKAKIKAI CO., LTD.), and 390 mg of test sample 3 were put on the filter paper 2. 10 ml of 3 degrees hard water were dripped over the test sample 3 so that the dripping period was 10 seconds or less, and filtrate was collected to sample bottle 4. The sample bottle 4 was changed to unused one, and the same procedures were repeated eight times in total every 25 minutes. Contents of the pesticidal active ingredient in any of collected filtrates were measured by liquid chromatography (internal standard method), elution rates were calculated by following formula.

Elution rate of the $N$th hard water titration (%)=Total amount of the pesticidal active ingredient containing in filtrates of from first to $N$th(mg)/Content of the pesticidal active ingredient containing in 390 mg of the Test sample(mg)×100

Provided that the N means any of integers of from 1 to 8. Results are described in Tables 3 to 5.

TABLE 3

| | the Present Granules of the invention | | | | | |
|---|---|---|---|---|---|---|
| | 1 | 2 | 3 | 4 | 5 | 6 |
| Elution rate of the 2nd hard water dripping (%) | 66.0 | 35.4 | 8.6 | 3.8 | 65.5 | 30.5 |

TABLE 4

| | the Present Granules of the invention 7 |
|---|---|
| Elution rate of the 1st hard water dripping (%) | 0.8 |
| Elution rate of the 2nd hard water dripping (%) | 2.8 |
| Elution rate of the 3rd hard water dripping (%) | 6.2 |
| Elution rate of the 4th hard water dripping (%) | 14.5 |
| Elution rate of the 5th hard water dripping (%) | 21.9 |
| Elution rate of the 6th hard water dripping (%) | 36.2 |
| Elution rate of the 7th hard water dripping (%) | 49.8 |
| Elution rate of the 8th hard water dripping (%) | 59.6 |

TABLE 5

| | the Comparative Granule | | | |
|---|---|---|---|---|
| | 1 | 2 | 3 | 4 |
| Elution rate of the 2nd hard water dripping (%) | 81.2 | 72.2 | 77.5 | 96.1 |

Production Examples 8 to 11 (Dust)

Raw materials described in the Table 6 are mixed at the weight ratio described in the Table 6, the Present dust of the invention 1 to 4 were obtained by pulverizing the mixture using centrifugal mill (manufactured by RETSCH GmbH).

In addition, figures in the Table 1 means parts by weight, and "balance" means residual amount of 100 parts by weight of whole amount.

TABLE 6

| | the Present dust of the invention | | | |
|---|---|---|---|---|
| | 1 | 2 | 3 | 4 |
| clothianidin fine powder | 0.72 | 0.72 | 0.72 | 0.72 |
| Sorpol 5080 | 1.0 | 1.0 | 1.0 | 1.0 |
| AKADAMA dextrin NDS | 4.0 | 4.0 | 4.0 | 4.0 |
| BENTONITE HODAKA | 20.0 | 20.0 | 20.0 | 20.0 |
| urea | 8.0 | 8.0 | 8.0 | 8.0 |
| ammoniun sulfate | 5.0 | 5.0 | 5.0 | 5.0 |
| RADIOLITE # 200 | 20.0 | 20.0 | 20.0 | 20.0 |
| Zeolite SK7A | 3.2 | 3.2 | 3.2 | 3.2 |
| Abscents 1000 | 1.0 | 3.0 | 5.0 | 10.0 |
| Tankaru NN200 | balance | balance | balance | balance |
| Total | 100.0 | 100.0 | 100.0 | 100.0 |

Explanations of ingredients described in above Table 6 are the same as those described in above Table 1.

Reference Production Example 6 (Water Non-Disintegrating Granule)

Raw materials described in the Table 7 are mixed at the weight ratio described in the Table 7, the Comparative Dusts 1 was obtained in the same manner as described in Production Examples 1 to 4

TABLE 7

| | the Comparative Dust 1 |
|---|---|
| clothianidin fine powder | 0.72 |
| Sorpol 5080 | 1.0 |
| AKADAMA dextrin NDS | 4.0 |
| BENTONITE HODAKA | 20.0 |
| urea | 8.0 |
| ammoniun sulfate | 5.0 |
| RADIOLITE # 200 | 20.0 |
| Mizuka Sieves EX122 | 3.0 |
| Tankaru NN200 | balance |
| Total | 100.0 |

Explanations of ingredients described in above Table 7 are described below.

Mizuka Sieves EX122: ZSM-5-type zeolite, total content of $SiO_2$ and $Al_2O_3$ 85.9% (measured value by ZSX Primus II), $SiO_2/Al_2O_3$ molar ratio 29.4, particle size 4.3 micrometer (measured value by Mastersizer 2000, wet measurement), specific surface area 420 $m^2/g$ (BET)

Explanations of remaining ingredients are as described above.

Test Example 2

Elution Test

Using the Present dusts of the invention 1 to 4 or the Comparative Dust 1 as the test sample 3, elution rates were calculated in the same manner as described in the Test Example 1.

TABLE 8

|  | the Present Dust of the invention | | | |
|---|---|---|---|---|
|  | 1 | 2 | 3 | 4 |
| Elution rate of the 2nd hard water dripping (%) | 57.2 | 31.2 | 16.0 | 9.7 |

TABLE 9

|  | the Comparative Dust 1 |
|---|---|
| Elution rate of the 2nd hard water dripping (%) | 72.2 |

The present invention provides the solid pesticidal formulation which sustains release of the pesticidal active ingredient contained therein and lasts such effect for a long time, by a simple method.

DESCRIPTION OF THE CODE

1 Glass funnel
2 Filter paper
3 Test sample
4 Sample bottle

The invention claimed is:

1. A sustained-release solid pesticidal formulation comprising a pesticidally active ingredient and a zeolite defined below, wherein the solubility in water of the pesticidally active ingredient is 100 to 100,000 mg/L, and wherein the zeolite has $SiO_2$ and $Al_2O_3$ in total of 90% by weight or more to the weight of the zeolite, has molar ratio of $SiO_2/Al_2O_3$ of 4 to 25, and has an average particle size of 10 μm or less.

2. The sustained-release solid pesticidal formulation according to claim 1, wherein the pesticidally active ingredient is a neonicotinoid type insecticidally active ingredient.

3. The sustained-release solid pesticidal formulation according to claim 2, wherein the neonicotinoid type insecticidally active ingredient is at least one neonicotinoid type insecticidally active ingredient selected from the group consisting of clothianidin, thiamethoxam, dinotefuran, imidacloprid, acetamiprid and thiacloprid.

4. The sustained-release solid pesticidal formulation according to claim 1, wherein the zeolite is Y type zeolite.

5. The sustained-release solid pesticidal formulation according to claim 1, which contains 0.01 to 30% by weight of the pesticidally active ingredient per 100% by weight of the formulation.

6. The sustained-release solid pesticidal formulation according to claim 1, which contains 0.1 to 20% by weight of the zeolite defined in claim 1 per 100% by weight of the formulation.

7. The sustained-release solid pesticidal formulation according to claim 1, wherein the ratio by weight of the pesticidally active ingredient and the zeolite defined in claim 1 is 1:0.1 to 1:30.

* * * * *